US 8,408,200 B2

(12) United States Patent
Clark et al.

(10) Patent No.: US 8,408,200 B2
(45) Date of Patent: Apr. 2, 2013

(54) FLOW RESISTANCE MODULATED AEROSOLIZED ACTIVE AGENT DELIVERY

(75) Inventors: Andrew Clark, Half Moon Bay, CA (US); Carlos Schuler, Cupertino, CA (US); Steve Paboojian, Menlo Park, CA (US)

(73) Assignee: Novartis AG, Basil (CH)

( * ) Notice: Subject to any disclaimer, the term of this patent is extended or adjusted under 35 U.S.C. 154(b) by 1577 days.

(21) Appl. No.: 09/414,384

(22) Filed: Oct. 7, 1999

(65) Prior Publication Data

US 2002/0168322 A1    Nov. 14, 2002

Related U.S. Application Data

(60) Provisional application No. 60/103,702, filed on Oct. 9, 1998.

(51) Int. Cl.
*A61M 16/00* (2006.01)
*A61M 15/00* (2006.01)
*A62B 9/02* (2006.01)

(52) U.S. Cl. ......... 128/203.15; 128/200.24; 128/203.12; 128/205.24

(58) Field of Classification Search .......... 424/45, 424/46; 128/200.14, 200.22, 200.23, 203.12, 128/204.11, 204.12, 204.23; 600/538, 532
See application file for complete search history.

(56) References Cited

U.S. PATENT DOCUMENTS

| | | | |
|---|---|---|---|
| 2,587,215 A | | 2/1952 | Priestly |
| 3,221,733 A | * | 12/1965 | Beasley .................. 128/200.14 |
| 3,788,310 A | | 1/1974 | Fleischmann |
| 3,837,341 A | | 9/1974 | Bell |
| 4,086,918 A | * | 5/1978 | Russo ............................ 600/538 |
| 4,106,503 A | | 8/1978 | Rosenthal et al. |
| 4,114,608 A | * | 9/1978 | Russo ............................ 600/538 |
| 4,170,228 A | * | 10/1979 | Elson et al. ................... 600/538 |
| 4,227,522 A | * | 10/1980 | Carris ...................... 128/203.15 |
| 4,231,375 A | * | 11/1980 | Boehringer et al. .......... 600/538 |
| 4,259,951 A | * | 4/1981 | Chernack et al. ............. 600/538 |
| 4,274,404 A | | 6/1981 | Molzan et al. |
| 4,284,083 A | * | 8/1981 | Lester ........................... 600/538 |
| 4,338,931 A | | 7/1982 | Cavazza |
| 4,391,283 A | * | 7/1983 | Sharpless et al. ............. 600/538 |
| 4,442,856 A | | 4/1984 | Betz |
| 4,444,202 A | * | 4/1984 | Rubin et al. .................. 600/538 |

(Continued)

FOREIGN PATENT DOCUMENTS

EP    0 808 635    11/1997
EP    0808635    11/1997

(Continued)

OTHER PUBLICATIONS

Elliott et al. (1987) Aust. Paediatr. 23: 293-297.

(Continued)

*Primary Examiner* — Annette Dixon
(74) *Attorney, Agent, or Firm* — Janah & Associates, P.C.

(57) ABSTRACT

The present invention is directed to methods and devices for delivering an active agent formulation to the lung of a human patient. The active agent formulation may be in dry powder form, it may be nebulized, or it may be in admixture with a propellant. The active agent formulation is delivered to a patient at a low inspiratory flow rate for an initial period of time to increase bioavailability of the active agent.

16 Claims, 7 Drawing Sheets

U.S. PATENT DOCUMENTS

| | | | | |
|---|---|---|---|---|
| 4,484,577 | A | 11/1984 | Sackner et al. | |
| 4,495,944 | A * | 1/1985 | Brisson et al. | 600/538 |
| 4,533,137 | A * | 8/1985 | Sonne | 482/13 |
| 4,558,710 | A * | 12/1985 | Eichler | 600/533 |
| 4,592,348 | A | 6/1986 | Waters et al. | |
| 4,627,432 | A | 12/1986 | Newell et al. | |
| 4,677,975 | A | 7/1987 | Edgar et al. | |
| 4,778,054 | A | 10/1988 | Newell et al. | |
| 4,811,731 | A | 3/1989 | Newell et al. | |
| 4,907,583 | A | 3/1990 | Wetterlin et al. | |
| 4,926,852 | A | 5/1990 | Zoltan et al. | |
| 4,955,371 | A | 9/1990 | Zamba et al. | |
| 4,984,158 | A * | 1/1991 | Hillsman | 128/200.14 |
| 4,991,745 | A | 2/1991 | Brown | |
| 5,027,806 | A | 7/1991 | Harrington et al. | |
| 5,033,655 | A | 7/1991 | Brown | |
| 5,040,527 | A | 8/1991 | Larson et al. | |
| 5,042,467 | A | 8/1991 | Foley | |
| 5,042,472 | A | 8/1991 | Bunin | |
| 5,161,524 | A | 11/1992 | Evans | |
| 5,167,506 | A * | 12/1992 | Killis et al. | 600/538 |
| 5,184,641 | A | 2/1993 | Kuhn | |
| 5,201,308 | A * | 4/1993 | Newhouse | 128/203.15 |
| 5,213,236 | A | 5/1993 | Brown et al. | |
| 5,284,133 | A | 2/1994 | Burns et al. | |
| 5,301,666 | A | 4/1994 | Lerk et al. | |
| 5,320,094 | A | 6/1994 | Laube et al. | |
| 5,327,883 | A * | 7/1994 | Williams et al. | 128/203.12 |
| 5,333,106 | A * | 7/1994 | Lanpher et al. | 600/538 |
| 5,339,995 | A | 8/1994 | Brown et al. | |
| 5,364,838 | A | 11/1994 | Rubsamen et al. | |
| 5,377,877 | A | 1/1995 | Brown et al. | |
| 5,385,140 | A | 1/1995 | Smith | |
| 5,408,994 | A | 4/1995 | Wass et al. | |
| 5,409,144 | A | 4/1995 | Brown | |
| 5,419,315 | A | 5/1995 | Rubsamen | |
| 5,435,301 | A | 7/1995 | Herold et al. | |
| 5,437,271 | A | 8/1995 | Hodson et al. | |
| 5,439,143 | A | 8/1995 | Brown et al. | |
| 5,447,151 | A | 9/1995 | Bruna et al. | |
| 5,458,135 | A * | 10/1995 | Patton et al. | 128/200.14 |
| 5,479,920 | A * | 1/1996 | Piper et al. | 128/204.23 |
| 5,483,954 | A | 1/1996 | Mecikalski | |
| 5,492,112 | A * | 2/1996 | Mecikalski et al. | 128/203.15 |
| 5,513,630 | A | 5/1996 | Century | |
| 5,522,380 | A | 6/1996 | Dwork | |
| 5,529,059 | A | 6/1996 | Armstrong et al. | |
| 5,533,505 | A | 7/1996 | Kallstrand et al. | |
| 5,542,412 | A | 8/1996 | Century | |
| 5,558,085 | A | 9/1996 | Rubsamen et al. | |
| 5,568,807 | A | 10/1996 | Mecikalski | |
| 5,568,910 | A | 10/1996 | Koehler et al. | 251/83 |
| 5,577,497 | A * | 11/1996 | Mecikalski et al. | 128/203.15 |
| 5,586,550 | A | 12/1996 | Ivri et al. | |
| 5,603,315 | A | 2/1997 | Sasso, Jr. | 128/204.18 |
| 5,617,845 | A | 4/1997 | Poss et al. | |
| 5,622,166 | A | 4/1997 | Eisele et al. | |
| 5,653,223 | A | 8/1997 | Pruitt | |
| 5,654,007 | A | 8/1997 | Johnson et al. | |
| 5,655,520 | A * | 8/1997 | Howe et al. | 128/203.12 |
| 5,666,945 | A * | 9/1997 | Davenport | 128/200.14 |
| 5,672,581 | A | 9/1997 | Rubsamen | |
| 5,692,492 | A | 12/1997 | Bruna et al. | |
| 5,692,496 | A | 12/1997 | Leith et al. | |
| 5,699,789 | A | 12/1997 | Hendricks | |
| 5,724,959 | A | 3/1998 | McAughey et al. | |
| 5,727,546 | A | 3/1998 | Clarke et al. | |
| 5,740,794 | A | 4/1998 | Smith et al. | |
| 5,775,320 | A | 7/1998 | Patton et al. | |
| 5,785,049 | A | 7/1998 | Smith et al. | |
| 5,813,401 | A | 9/1998 | Radcliff et al. | |
| 5,823,183 | A | 10/1998 | Casper et al. | |
| 5,826,571 | A | 10/1998 | Casper et al. | |
| 5,826,633 | A | 10/1998 | Parks et al. | |
| 5,855,202 | A | 1/1999 | Andrade | |
| 5,865,173 | A * | 2/1999 | Froehlich | 128/204.23 |
| 5,873,358 | A | 2/1999 | Gonda et al. | |
| 5,875,776 | A | 3/1999 | Vaghefi | |
| 5,881,719 | A | 3/1999 | Gottenauer et al. | |
| 5,884,623 | A | 3/1999 | Gonda et al. | |
| 5,896,853 | A | 4/1999 | Howlett | |
| 5,921,237 | A | 7/1999 | Eisele et al. | |
| 5,922,354 | A | 7/1999 | Johnson et al. | |
| 5,941,240 | A | 8/1999 | Gonda et al. | |
| 5,975,076 | A | 11/1999 | Yianneskis et al. | |
| 5,983,893 | A | 11/1999 | Wetterlin | |
| 5,988,163 | A | 11/1999 | Casper et al. | |
| 5,993,421 | A | 11/1999 | Kriesel | |
| 6,006,747 | A | 12/1999 | Eisele et al. | |
| 6,012,454 | A | 1/2000 | Hodson et al. | |
| 6,029,661 | A | 2/2000 | Whaley et al. | |
| 6,029,663 | A | 2/2000 | Eisele et al. | |
| 6,032,667 | A | 3/2000 | Heinonen | 128/205.24 |
| 6,055,979 | A | 5/2000 | Fuchs | |
| 6,055,980 | A | 5/2000 | Mecikalski et al. | |
| 6,062,214 | A * | 5/2000 | Howlett | 128/200.23 |
| 6,065,472 | A | 5/2000 | Anderson et al. | |
| 6,067,984 | A | 5/2000 | Piper | 128/205.24 |
| 6,070,573 | A * | 6/2000 | Howe et al. | 128/200.14 |
| 6,076,523 | A | 6/2000 | Jones et al. | |
| 6,085,753 | A | 7/2000 | Gonda et al. | |
| 6,089,228 | A | 7/2000 | Smith et al. | |
| 6,095,134 | A | 8/2000 | Sievers et al. | |
| 6,102,036 | A | 8/2000 | Slutsky et al. | |
| 6,105,574 | A | 8/2000 | Jahnsson | |
| 6,109,261 | A | 8/2000 | Clarke et al. | |
| 6,116,237 | A | 9/2000 | Schultz et al. | |
| 6,116,238 | A | 9/2000 | Jackson et al. | |
| 6,116,239 | A | 9/2000 | Volgyesi | |
| 6,131,571 | A | 10/2000 | Lampotang et al. | 128/204.21 |
| 6,138,673 | A | 10/2000 | Shepherd | |
| 6,142,146 | A | 11/2000 | Abrams et al. | |
| 6,170,482 | B1 * | 1/2001 | Howlett | 128/200.23 |
| 6,176,237 | B1 | 1/2001 | Wunderlich et al. | 128/203.12 |
| 6,182,655 | B1 | 2/2001 | Keller et al. | |
| 6,186,142 | B1 | 2/2001 | Schmidt et al. | 128/204.23 |
| 6,253,764 | B1 | 7/2001 | Calluaud | 128/204.18 |
| 6,422,234 | B1 * | 7/2002 | Bacon | 128/200.14 |
| 6,655,379 | B2 * | 12/2003 | Clark et al. | 128/203.12 |

FOREIGN PATENT DOCUMENTS

| | | |
|---|---|---|
| EP | 692990 | 9/1998 |
| EP | 0714314 | 10/1998 |
| EP | 0805696 | 3/2000 |
| GB | 1598053 | 9/1981 |
| HU | 181864 | 11/1983 |
| HU | P9602818 | 2/1997 |
| HU | 213685 | 9/1997 |
| HU | 217917 | 5/2000 |
| WO | WO 91/14422 | 2/1991 |
| WO | WO95/24183 | 9/1995 |
| WO | WO95/34337 | 12/1995 |
| WO | WO 96/09085 | 2/1996 |
| WO | WO 96/32149 | 2/1996 |
| WO | WO 97/20589 | 6/1997 |
| WO | WO97/40819 | 11/1997 |
| WO | WO 97 40819 | 11/1997 |
| WO | WO98/32479 | 7/1998 |
| WO | WO99/27987 | 6/1999 |
| WO | WO99/46055 | 6/1999 |
| WO | WO99/47196 | 9/1999 |
| WO | WO00/21594 | 4/2000 |

OTHER PUBLICATIONS

Elliott et al., Aust. Paediatr. J., p. 293-297. (Feb. 28, 1987).

Barrowcliffe et al., "The In-Vitro Evaluation of a Novel Multi-Dose Dry Powder", The Aerosol Society, 1996; pp. 82-85.

Chrystyn, "The Diskus Inhaler, A Review of its Pharmaceutical and Clinical Performance", Clinical Drug Investigations, 1999; pp. 287-296, vol. 18, No. 4.

Conway et al., "Comparison of Peak Pressure Drops Through Powder Inhalers During Inspiration at Maximum Flow Rate", 1996; pp. 153, A59.

Malton et al., "A Comparison of In-Vitro Drug Delivery from Salbutamol Diskus and Terbutaline Turbohaler Inhalers", J. Pharm., Med., 1996; pp. 35-48, vol. 6.

Malton et al., "A Comparison of In-Vitro Drug Delivery from Two Multidose Powder Inhalation Devices", Euro. J. Clinical Research, 1995; pp. 177-193, vol. 7.

Newhouse et al., "Clickhaler (a novel Dry Powder Inhaler) Provides Similar Bronchodilation to Pressurized Metered-Dose Inhaler, Even at Low Flow Rates", Clinical Investigation, pp. 952-956, 1999.

Prime et al., "The Flixotide Diskus, a New Multi Dose Powder Inhaler—In-Vitro Evaluation Using an Inhalation Simulator", J. Aerosol Med., 1995; pp. P137.

Clark et al., "The Relationship Between Powder Inhaler Resistance and Peak Inspiratory Conditions in Healthy Volunteers—Implications for In Vitro Testing", Journal of Aerosol Medicine, 1993; pp. 99-110, vol. 6 No. 2.

Hill, "Characteristics of an Active, Multiple Dose Dry Powder Inhaler", Respiratory Drug Delivery IV, 1994; pp. 109-116.

Dolovich, "Physical Principles Underlying Aerosol Therapy", Journal of Aerosol Medicine, 1989; pp. 171-186, vol. 2 No. 2.

Clark, "Effect of Powder Inhaler Resistance Upon Inspiratory Profiles in Health and Disease", Respiratory Drug Delivery IV, 1994; pp. 117-123.

Ross et al., "Effect of Inhalation Flow Rate on the Dosing Characteristics of Dry Powder Inhaler (DPI) and Metered Dose Inhaler (MDI) Products", Journal of Aerosol Medicine, 1996; pp. 215-226, vol. 9 No. 2.

Lawford et al., "Pressurized Aerosol Inhaler Techniques: How Important are Inhalation from Residual Volume, Inspiratory Flow Rate and the Time Interval Between Puffs?", J. Dis. Chest, 1983; 77, pp. 276-281.

\* cited by examiner

FLOW RESISTANCE MODULATED AEROSOLIZED ACTIVE AGENT DELIVERY

This application claims priority to U.S. Provisional Patent Application Ser. No. 60/103,702 which was filed on Oct. 9, 1998.

FIELD OF THE INVENTION

The present invention is related to the pulmonary delivery of an active agent formulation. More particularly, it is a method and device for pulmonary delivery of an active agent formulation for increased systemic bioavailability of the active agent via absorption in the deep lung. The bioavailability is increased by modulating the flow rate of the aerosolized active agent in a manner that is independent of patient instruction and flow rate monitoring.

BACKGROUND OF THE INVENTION

Effective delivery to a patient is a critical aspect of any successful drug therapy. Various routes of delivery exist, and each has its own advantages and disadvantages. Oral drug delivery of pills, capsules, elixirs, and the like is perhaps the most convenient method, but many drugs are degraded in the digestive tract before they can be absorbed. Subcutaneous injection is frequently an effective route for systemic drug delivery, including the delivery of proteins, but enjoys a low patient acceptance. Since injection of drugs, such as insulin, one or more times a day can frequently be a source of poor patient compliance, a variety of alternative routes of administration have also been developed, including transdermal, intranasal, intrarectal, intravaginal, and pulmonary delivery.

Of particular interest, pulmonary drug delivery relies on inhalation of an active agent formulation by the patient so that active drug within the dispersion can reach the distal (alveolar) regions of the lung. This may be accomplished using a patient driven device where it is the inspiratory flow that aerosolizes the active agent formulation or using a drug dispersion or aerosol device that uses a compressed gas or propellant to aerosolize and deliver the active agent formulation.

It has been found that certain drugs are readily absorbed through the alveolar region directly into blood circulation. Pulmonary delivery is particularly promising for the delivery of proteins and polypeptides which are difficult to deliver by other routes of administration. Such pulmonary delivery is effective both for systemic delivery and for localized delivery to treat diseases of the lungs.

Elliot et al, Aust. Paediatr. J. (1987)23:293-297 described the nebulized delivery of semi-synthetic human insulin to the respiratory tracts of six diabetic children and determined that it was possible to control diabetes in these children, although the efficiency of absorption was low (20-25%) as compared to subcutaneous delivery. Laube et al., U.S. Pat. No. 5,320,094, noting Elliot and a number of other studies, stressed that although insulin had been delivered to the lung, none of the patients had responded to the pulmonary insulin therapy sufficient for lowering of blood glucose levels to within a normal range. Laube et al. hypothesized that this problem resulted from the loss of drug in the delivery system and/or in the oropharynx as a result of the method of delivery and that the maximization of deposition within the lungs should improve glucose control in the blood. In order to achieve maximum delivery, Laube et al controlled the inspiratory flow rate at the time of aerosol inhalation at flow rates of less than 30 liters/minute and, preferably about 17 liters/minute. The delivery system included a medication chamber for receiving the insulin, an outlet aperture through which the insulin was withdrawn, and a flow rate limiting aperture to control the inspiratory flow rate.

Commonly assigned U.S. Patent Application No. 60/078,212 tested the above hypothesis and noted that pulmonary delivery of insulin at less than 17 liters per minute provided for increased blood levels of insulin in a shorter time period than higher inspiratory flow rates.

Rubsamen et al, U.S. Pat. Nos. 5,364,838 and 5,672,581 describe the delivery of a measured amount of aerosolized insulin. The insulin is automatically released into the inspiratory flow path in response to information obtained from determining the inspiratory flow rate and inspiratory volume of a patient. A monitoring device continually sends information to a microprocessor, and when the microprocessor determines that an optimal point in the respiratory cycle is reached, the microprocessor actuates the opening of a valve allowing release of insulin. The inspiratory flow rate is in the range of from about 0.1 to 2.0 liters/second and the volume is in the range of from about 0.1 to 0.8 liters.

WO 97/40819 describes slow inspiratory flow rates as being key to increased drug delivery and deposition of drugs delivered via the pulmonary route. In order to obtain the target flow rates (15-60 liters per minute), the device resistance was designed to be within the 0.12 to 0.21 (cm $H_2O)^2$. EPO 692990 B1 describes deagglomerators for dry powder inhalers and notes that it is desirable to reduce the airflow rate dependence of the delivered dose and/or respirable fraction of an inhaled powder aerosol. The deagglomerators respond to increasing flow rates to vary the geometry of a channel through which powder laden air passes resulting in a lesser pressure drop increase than would be seen in the absence of the variable geometry and that provide for more effective deagglomeration over a range of flow rates.

We have now determined that, in order to effectively deliver an active agent via the pulmonary route in a comfortable and reproducible manner, it is desirable to maintain a low initial flow rate followed by a period of higher flow.

SUMMARY OF THE INVENTION

Accordingly, in one aspect, the present invention is directed to a device for delivering an aersolized active agent formulation to the lungs of a human patient. The device comprises a flow resistance modulator that modulates resistance to the flow of the aerosolized active agent formulation to produce an initial target flow rate of the aerosolized active agent formulation. The flow resistance modulator modulates the resistance in a manner that is independent of flow rate monitoring and patient instruction.

In another aspect, the present invention is directed to a method for delivering an active agent formulation to the lungs of a human patient. The method comprises providing the aerosolized active agent formulation with high flow resistance for an initial period followed by a period of lower flow resistance.

DETAILED DESCRIPTION OF THE INVENTION

Figure 1:
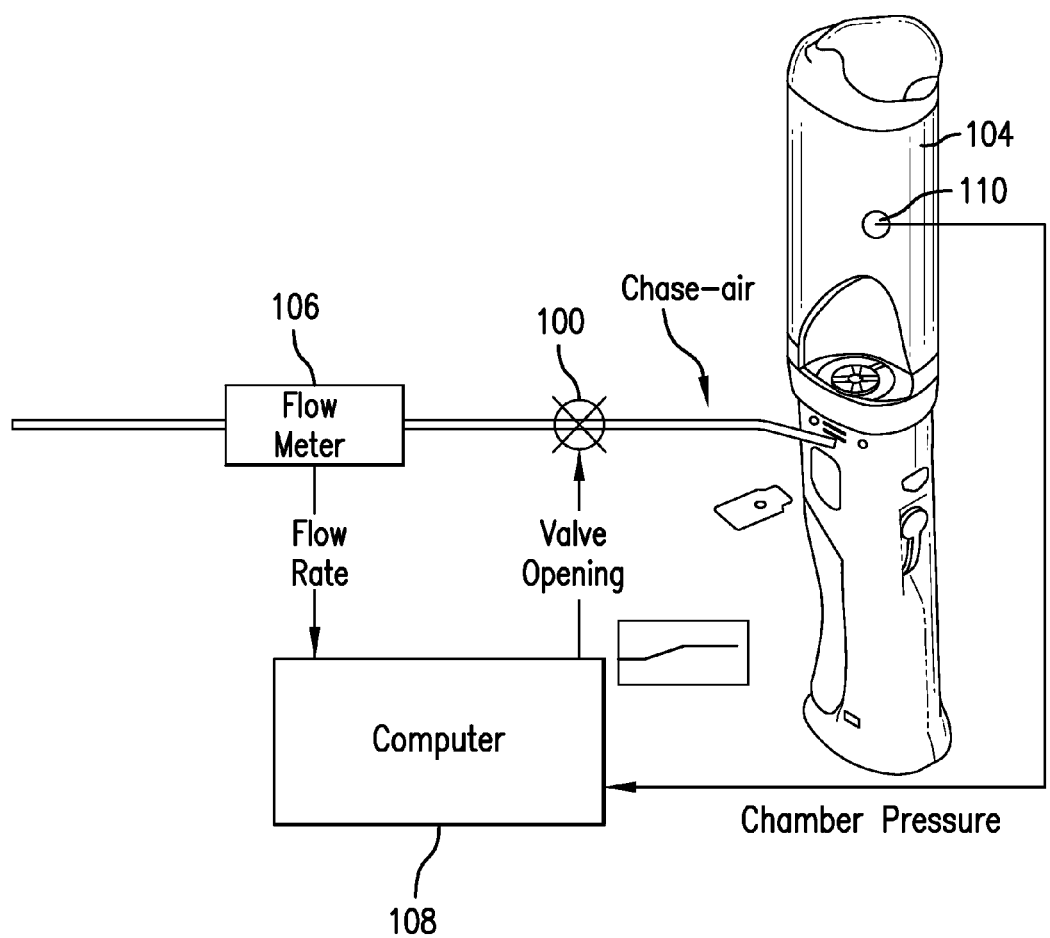
FIG. 1 is a schematic of an embodiment of a dry powder active agent formulation delivery device of the invention.

The present invention provides a method and device for the pulmonary delivery of an active agent formulation where flow resistance of the active agent formulation is varied with time. The invention is surprising in that it provides for increased blood levels of active agent in a comfortable and reproducible manner.

DEFINITIONS

"Active agent" as described herein includes an agent, drug, compound, composition of matter or mixture there which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system the central nervous system. Suitable agents may be selected from, for example, polysaccharides, steroid, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporin, granulocyte colony stimulating factor (GCSF), alpha-1 proteinase inhibitor, elcatonin, granulocyte macrophage colony stimulating factor (GCSF), growth hormone, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin analogs including octreotide, vasopressin analog, follicle stimulating hormone (FSH), insulin-like growth factor, insulintropin, interleukin-1 receptor antagonist, interleukin-3, interleukin-4, interleukin-6, interleukin-10, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal permeability increasing protein (BPI), anti-CMV antibody, interleukin-1 receptor, 13-cis retinoic acid, pentamidine isethiouate, albuterol sulfate, metaproterenol sulfate, beclomethasone diprepionate, triamcinolone acetamide, budesonide acetonide, ipratropium bromide, flunisolide, cromolyn sodium, ergotamine tartrate and the analogues, agonists and antagonists of the above. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

"Aerosolized active agent formulation" means the active agent as defined above in a formulation that is suitable for pulmonary delivery. The aerosolized active agent formulation may be in the dry powder form, it may be a solution, suspension or slurry to be nebulized, or it may be in admixture with a suitable low boiling point, highly volatile propellant. It is to be understood that more than one active agent may be incorporated into the aerosolized active agent formulation and that the use of the term "agent" in no way excludes the use of two or more such agents.

The "inspiratory flow rate" is the flow rate at which the aerosolized active agent formulation is delivered.

The amount of active agent in the aerosolized active agent formulation will be that amount necessary to deliver a therapeutically effective amount of the active agent to achieve the desired result. In practice, this will vary widely depending upon the particular agent, the severity of the condition, and the desired therapeutic effect. However, the device is generally useful for active agents that must be delivered in doses of from 0.001 mg/day to 100 mg/day, preferably 0.01 mg/day to 50 mg/day.

The present invention is based at least in part on the unexpected observation that when an active agent is delivered to a patient at an initially low inspiratory flow rate, the bioavailability of the active agent increases as opposed to when the active agent is delivered at a constant but higher inspiratory flow rate.

Active agent formulations suitable for use in the present invention include dry powders, solutions, suspensions or slurries for nebulization and particles suspended or dissolved within a propellant. Dry powders suitable for use in the present invention include amorphous active agents, crystalline active agents and mixtures of both amorphous and crystalline active agents. The dry powder active agents have a particle size selected to permit penetration into the alveoli of the lungs, that is, preferably 10 µm mass median diameter (MMD) or less, preferably less than 7.5 µm, and most preferably less than 5 μm, and usually being in the range of 0.1 μm in diameter. The delivered dose efficiency (DDE) of these powders is >30%, usually>40%, preferably >50 and often>60% and the aerosol particle size distribution is about 1.0-5.0 μm mass median aerodynamic diameter (MMAD), usually 1.5-4.5 μm MMAD and preferably 1.5-4.0 μm MMAD. These dry powder active agents have a moisture content below about 10% by weight, usually below about 5% by weight, and preferably below about 3% by weight. Such active agent powders are described in WO 95/24183 and WO 96/32149, which are incorporated by reference herein. However, it may be possible to deliver larger sized particles, such as those with MMD's between 10 and 30 μm so long as the MMAD's of the particles are below 5.0 μm. Such particles are described, for example, in PCT publications WO 97/44013 and WO 98/31346 the disclosures of which are incorporated herein by reference.

Dry powder active agent formulations are preferably prepared by spray drying under conditions which result in a substantially amorphous powder. Bulk active agent, usually in crystalline form, is dissolved in a physiologically acceptable aqueous buffer, typically a citrate buffer having a pH range from about 2 to 9. The active agent is dissolved at a concentration from 0.01% by weight to 1% by weight, usually from 0.1% to 0.2%. The solutions may then be spray dried in a conventional spray drier available from commercial suppliers such as Niro A/S (Denmark), Buchi (Switzerland) and the like, resulting in a substantially amorphous powder. These amorphous powders may also be prepared by lyophilization, vacuum drying, or evaporative drying of a suitable active agent solution under conditions to produce the amorphous structure. The amorphous active agent formulation so produced can be ground or milled to produce particles within the desired size range. Dry powder active agents may also be in a crystalline form. The crystalline dry powders may be prepared by grinding or jet milling the bulk crystalline active agent.

The active agent powders of the present invention may optionally be combined with pharmaceutical carriers or excipients which are suitable for respiratory and pulmonary administration. Such carriers may serve simply as bulking agents when it is desired to reduce the active agent concentration in the powder which is being delivered to a patient, but may also serve to improve the dispersability of the powder within a powder dispersion device in order to provide more efficient and reproducible delivery of the active agent and to improve handling characteristic of the active agent such as flowability and consistency to facilitate manufacturing and powder filling. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamine hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffinose, maltodextrins, glycine, sodium citrate, human serum albumin and mannitol.

The dry powder active agent formulations may be delivered using Inhale Therapeutic Systems' dry powder inhaler as described in WO 96/09085 which is incorporated herein by reference, but adapted to control the flow resistance as described below. The dry powders may also be delivered using a metered dose inhaler as described by Laube et al in U.S. Pat. No. 5,320,094, which is incorporated by reference herein or by a patient driven device such as that described in U.S. Pat. No. 4,338,931 which is incorporated by reference herein.

Nebulized solutions may be prepared by aerosolizing commercially available active agent formulation solutions. These solutions may be delivered by a dosimeter, that is a nebulizer that delivers an aerosol in a controlled, bolus dose, such as the Raindrop, produced by Puritan Bennett, the use of which is described by Laube et al. Other methods for delivery of solutions, suspensions or slurries are described by Rubsamen et al, U.S. Pat. No. 5,672,581. A device that uses a vibrating, piezoelectric member is described in Ivri et al, U.S. Pat. No. 5,586,550, which is incorporated by reference herein.

Propellant systems may include an active agent dissolved in a propellant or particles suspended in a propellant. Both of these types of formulations are described in Rubsamen et al, U.S. Pat. No. 5,672,581, which is incorporated herein by reference.

In order to obtain the increased bioavailabilies of active agent, the devices described above must be modified in order to restrict the initial inspiratory flow rate of the active agent formulation. We have found that once an initial period of low inspiratory flow rate has been established, the restriction can be relieved and a higher flow rate is permissible. If the higher flow rate is not established, the patient will become frustrated and will cease to inhale.

According to the invention, a flow rate of less than about 15 liters per minute, preferably less than 10 liters per minute and often between about 5 and 10 liters per minute will be established for a period of less than about 10 seconds, preferably less than 5 seconds and often between about 3 and 5 seconds. Following this initial period of limited flow rate, the flow rate restriction will be released and the flow rate will be the normal inspiratory flow rate of the patient. This flow rate is between about 15 and 80 liters per minute, usually between about 15 and 60 liters per minute and often between about 15 and 30 liters per minute. In order to accomplish this, a flow resistance modulator will be incorporated into the device. A pressure sensor in the device will determine the onset of inhalation. The flow resistance modulator will be set to a high resistance, between about 0.4 and 2 $(cm\ H_2O)^2$ SLM (where SLM is liters per minute at standard temperature and pressure), usually between about 0.4 and 1.5 $(cm\ H_2O)$ SLM and often between about 0.5 and 1.0 $(cm\ H_2O)^2$/SLM to obtain the flow rate described above. Once the initial period of limited flow has passed, as determined by the pressure sensor and the pre-established time period, the flow resistance modulator will be reset such that it will provide little if any resistance to the flow. This resistance will be between about 0 and 0.3 $(cm\ H_2O)^2$ SLM usually between 0 and 0.25 $(cm\ H_2O)$ SLM and often between 0 and 0.2 $(cm\ H_2O)^2$ SLM. Accordingly, the normal, comfortable inspiratory flow rate of the patient will be established. An exemplary system for flow rate modulation is shown in FIG. 1. In this system, the flow rate modulator is a valve (100) placed on the intake air manifold (102) to the device (104) to control the flow rate of the intake air. Flow meter (106) and computer (108) are only used to assess patient behavior in response to flow restriction for investigational purposes. Pressure sensor (110) measures the onset of inhalation and triggers the opening of valve (100). Although the flow rate modulator in this case is shown to be a valve driven by a microprocessor, simple mechanical valving systems may be used as well. Further, in order to detect onset of inhalation, either a flow sensor or a pressure sensor could be used.

According to a further feature of this invention, is that it has been found that impaction in the throat by particles is proportional to the flow rate and the square of the aerodynamic diameter according to the following equation:

I=kd-Q

I=number of particles impacting in the throat k=proportionality constant d=MMAD of the particles Q=flow rate According to the above equation, it is possible to deliver larger particles using the low initial flow rates of the current invention without raising the number of particles that impact in the throat provided the majority of the active agent is delivered during the low flow rate period. Initially, then, when the flow rate is low and the concentration of the aerosol is high, that is, the number of particles in the aerosol is at its peak, the particles will be preferentially delivered to the deep lung rather than being impacted in the throat and the bioavailability of the active agent will be increased.

Figure 2:
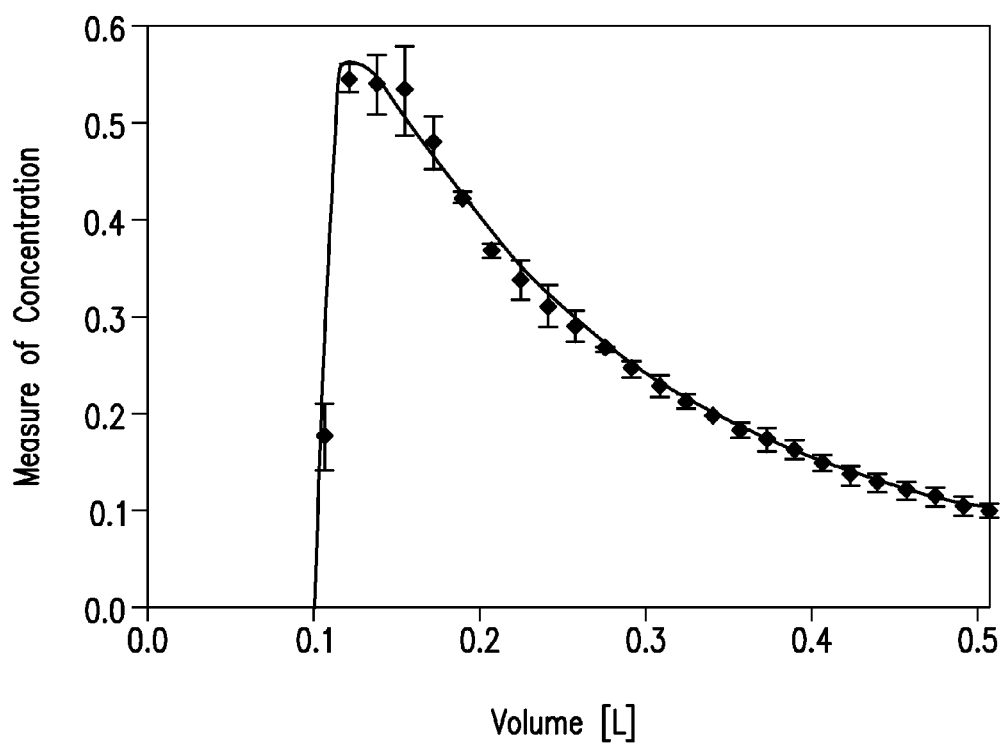
FIG. 2 is a graph of the concentration of the aerosol delivered from the device of FIG. 1.
Figure 3:
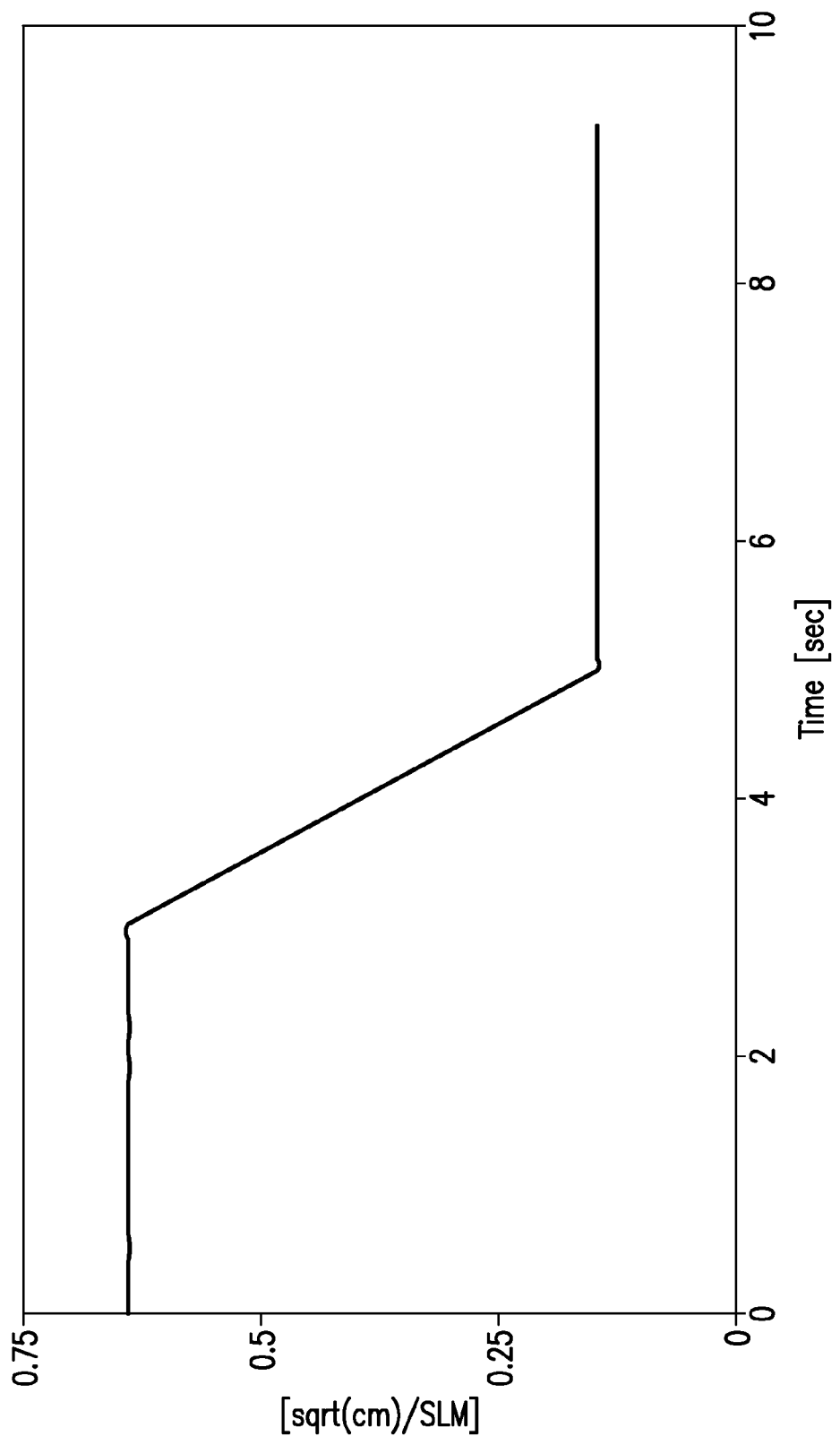
FIG. 3 is a graph of the resistance of the flow resistance modulator of the device of FIG. 1 as function of time.
Figure 4:
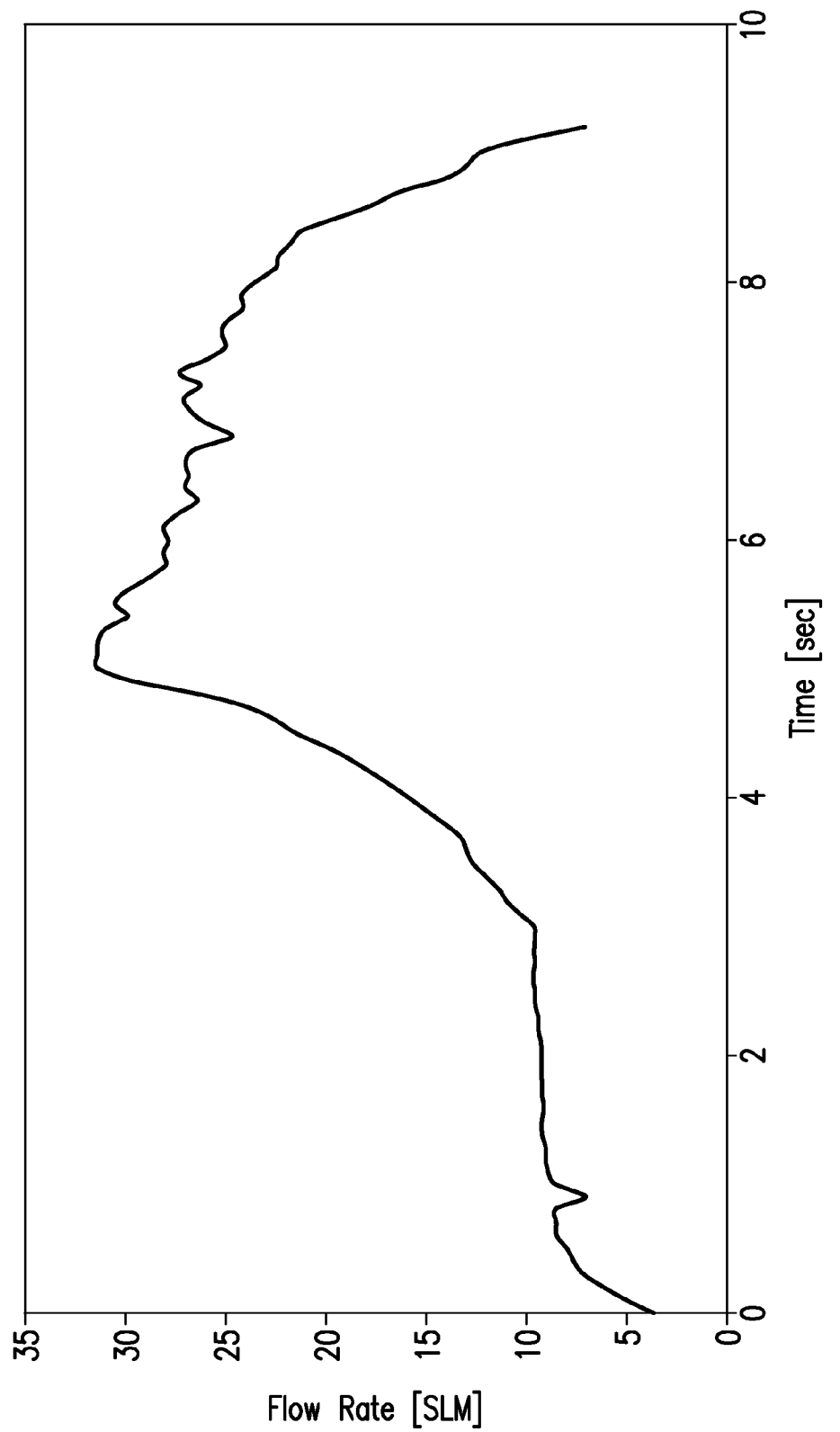
FIG. 4 is a graph of the resistance of the flow rate corresponding to the resistance shown in FIG. 3.
Figure 5:
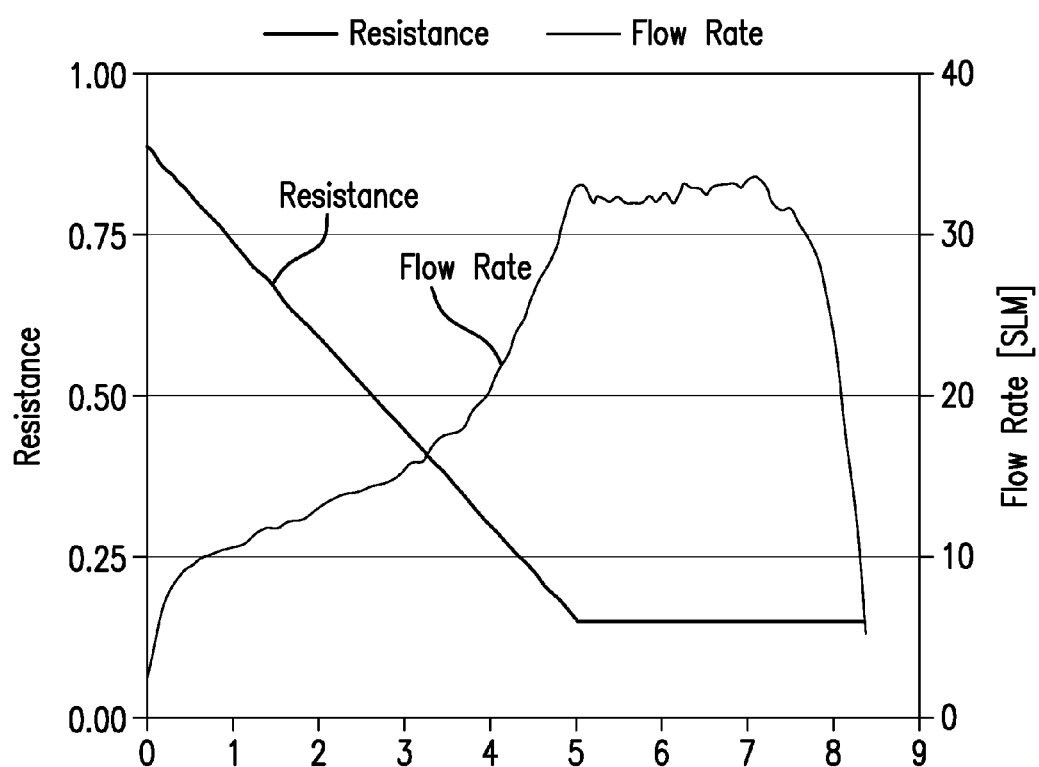
FIG. 5 are superimposed graphs a flow modulator of the invention and the corresponding flow rate of the associated device.

The aerosol concentration exiting the device of FIG. 1 is shown in FIG. 2. For a 0.5 liter aerosol, the graph shows that the concentration of the first 0.1 to 0.2 liters is the highest and that after that the concentration tapers off. It is therefore important to deliver the initial portion of the aerosol at a low flow to avoid throat impaction and increase bioavailability. The resistance profile of a flow rate modulator to accomplish this is shown in FIG. 3. The resistance is high (0.65 (cm $H_2O)^2$ SLM) for an initial 3 second time period, the valve is then opened and the resistance transitions to the normal resistance of the device (in this case 0.15 (cm $H_2O)^2$/SLM. As can be seen from the flow rates of FIG. 4, the inspiratory flow rate in the initial period is about 10 SLM and then transitions up to about 25-30 SLM. The resistance profile of a further flow rate modulator of the invention and its associated flow rate profile is shown in FIG. 5. The resistance transitions from high to low (0.9 to 0.20 (cm $H_2O)^2$/SLM) for an initial 5 second time period. As can be seen from the flow rates of FIG. 5, the inspiratory flow rate in the initial 3 second period is less than 20 SLM and then transitions up to about 30 SLM. In both of these cases, since the concentration of the aerosol in the first 0.1 to 0.2 liters is the greatest, the majority of the active agent is delivered in the initial 3 second time period. This increases the deep lung delivery and thus the bioavailability of the active agent.

The following examples are illustrative of the present invention. They are not to be construed as limiting the scope of the invention. Variations and equivalents of the examples will be apparent to those of skill in the art in light of the present disclosure, the drawings and the claims herein.

EXAMPLES

Example 1

Figure 6:
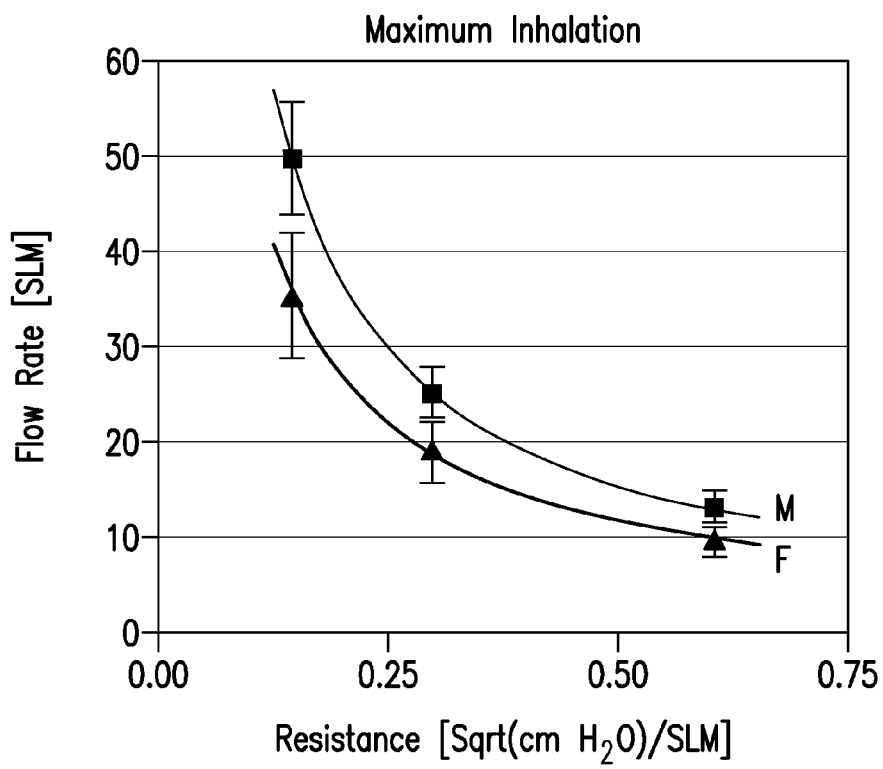
FIG. 6 is a graph of the inhalation rates of patients using the device of FIG. 1 at varying flow resitances using maximum inhalation effort.
Figure 7:
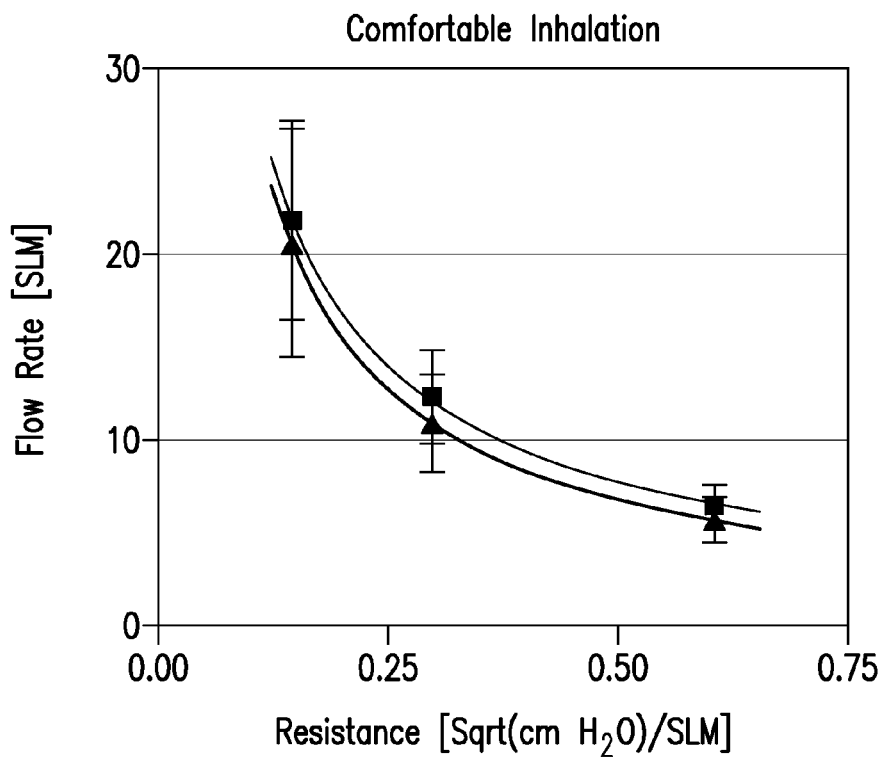
FIG. 7 is a graph of the inhalation volumes of patients using the device of FIG. 1 at varying flow resitances using maximum inhalation effort.
Figure 8:
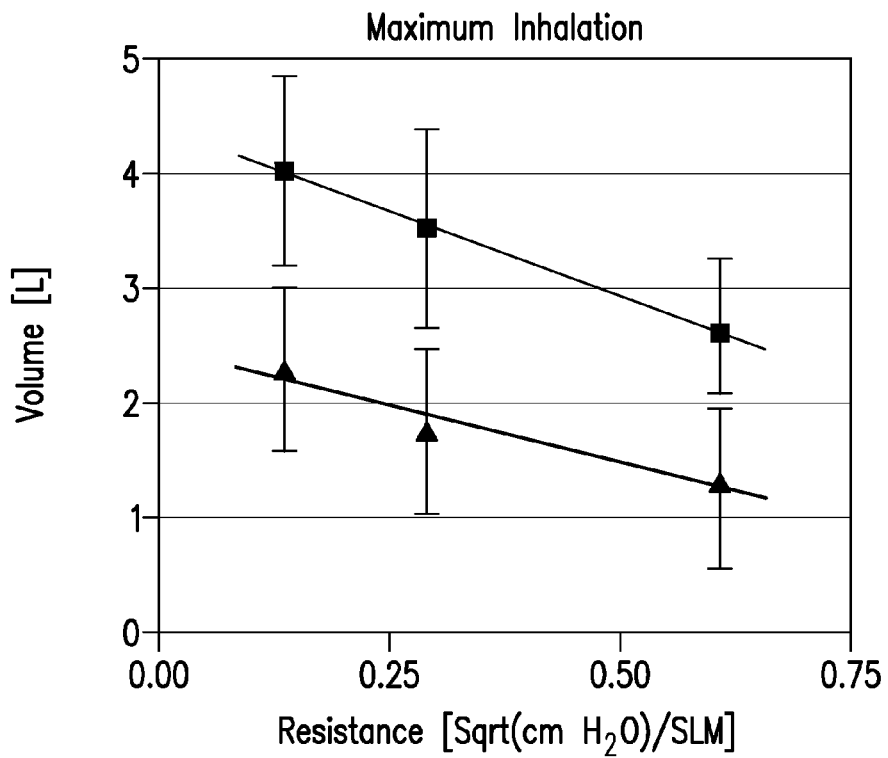
FIG. 8 is a graph of the comfortable inhalation rates of patients using the device of FIG. 1 at varying flow resitances.
Figure 9:
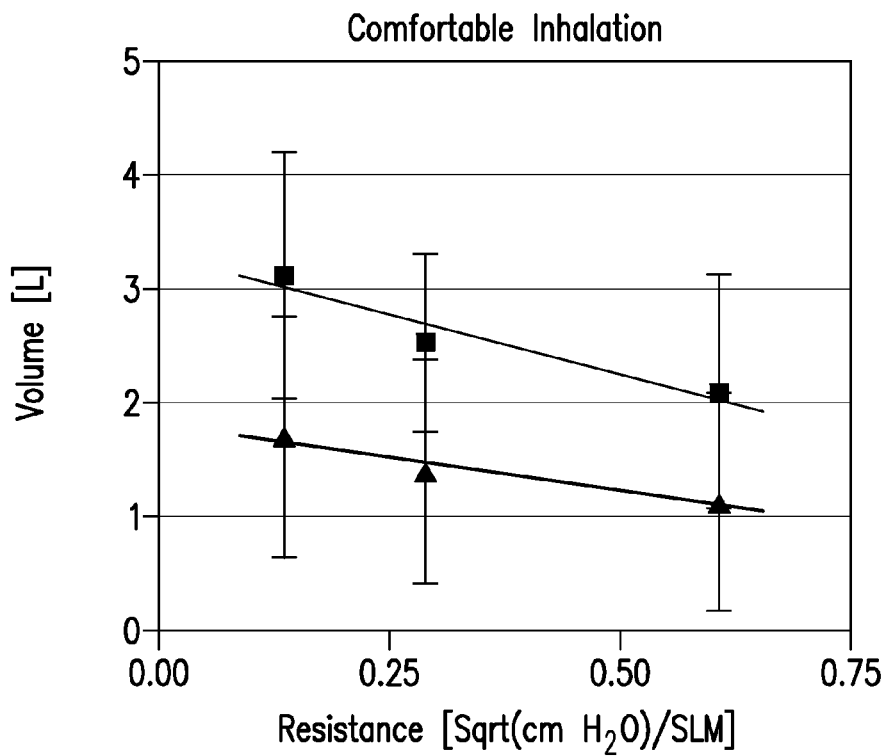
FIG. 9 is a graph of the inhalation volumes of patient using the device of FIG. 1 at varying flow resitances at a comfortable inhalation rate.

In order to determine the relationship of flow resistance to flow rate, 10 volunteers, 5 males (M) and 5 females (F) were asked to breathe against 3 different resistances and instructed to inhale both maximally and at a comfortable rate. The results are shown in FIGS. 6-9. FIGS. 6 and 7 are the flow rates for maximal and comfortable inhalation rates for males and females. FIGS. 8 and 9 show the volumes of aerosol inhaled at the maximum and comfortable inhalation rates and resistances described above.

The resistance to comfortably maintain a 10 liter per minute flow rate is about 0.3 (cm $H_2O)^2$ SLM. Further, the inspiratory volume of aerosol delivered at higher flow resistances drops because inspiration becomes more and more difficult and less comfortable as resistance increases. In fact, if resistance is decreased after the initial aerosol delivery period of high resistance, the inspiratory volume will not decrease significantly over the volume delivered at a constant low flow resistance delivery rate.

Example 2

Materials and Methods

Materials

Crystalline human zinc insulin, 26.3 U/mg is obtained from Eli Lilly and Company, Indianapolis, Ind. and found to be>99% pure as measured by reverse phase HPLC, USP mannitol is obtained from Roquette Corporation (Gurnee, Ill.). Glycine was purchased from Sigma Chemical Company (St. Louis, Mo.). Sodium citrate dihydrate, USP is obtained from J. T. Baker (Phillipsburg, N.J.).

Powder Production

Insulin powders are made by dissolving bulk crystalline insulin in sodium citrate buffer containing mannitol and glycine to give final solids concentration of 7.5 mg/ml and pH of 6.7±0.3. The spray dryer is operated with an inlet temperature between 110° C. and 120° C. and a liquid feed rate of 5 ml/min, resulting in an outlet temperature between 70° C. and 80° C. The solutions are then filtered through a 0.22 µm filter and spray dried in a Buchi Spray Dryer to form a fine white amorphous powder. The resulting powders are stored in tightly capped containers in a dry environment (<10% RH).

Powder Analysis

The particle size distribution of the powders is measured by liquid centrifugal sedimentation in a Horiba CAPA-700 Particle Size Analyzer following dispersion of the powders in Sedisperse A-11 (Micrometrics, Norcross, Ga.). The moisture content of the powders is measured by the Karl Fischer technique using a Mitsubishi CA-06 Moisture Meter. The aerosol particle size distribution is measured using a cascade impactor (Graseby Andersen, Smyrna, Ga.). The delivered dose efficiency (DDE) is evaluated using the Inhale Therapeutic Systems aerosol devices, similar to those described in WO96/09085. The DDE is defined as the percentage of the nominal dose contained within a blister package that exited the mouthpiece of the aerosol device and was captured on a glass fiber filter (Gelman, 47 mm diameter) through which a vacuum was drawn (30 L/min) for 2.5 seconds following device actuation. DDE is calculated by dividing the mass of the powder collected on the filter by the mass of the powder in the blister pack.

The integrity of insulin before and after powder processing is measured against a reference standard of human insulin by redissolving weighed portions of powder in distilled water and comparing the redissolved solution with the original solution put into the spray dryer. Retention time and peak area by rpHPLC are used to determine whether the insulin molecule had been chemically modified or degraded in the process. UV absorbance was used to determine insulin concentration (at 278 nm) and presence of absence of insoluble aggregates (at 400 nm). In addition, the pHs of the starting and reconstituted solutions are measured. The amorphous nature of the insulin powder is confirmed by polarized light microscopy.

In Vivo Testing

In order to examine the effect of changes in the rate of inhalation on the bioavailability of inhaled insulin, 24 individuals are dosed with 2 mg of insulin using the system shown in FIG. 1. Each treatment will consist of two inhalations of 1 mg each. Inhalers are Inhale Therapeutic Systems Inhalers (San Carlos, Calif.) as described in U.S. Pat. No. 5,740,794, which is incorporated by reference herein. The treatments are:

A. Inhalation administration of insulin with a particle size of 3.6μ MMAD (large PSD), utilizing the standard breathing maneuver and inhaler (no ramp).

B. Inhalation administration of insulin with a particle size of 3.6μ MMAD (large PSD), with the inhalation rate limited to approximately 10 liters per minute by the system shown in FIG. 1 (ramp).

C. Inhalation administration of insulin with a particle size of 2.6μ MMAD (small PSD), with the inhalation rate limited to approximately 10 liters per minute by the system shown in FIG. 1 (ramp).

The insulin dry powder formulations have average particle diameters of less than 5 microns. The inhaler disperses the powders and produces aerosol clouds (puffs) of medication which are held in a volume of approximately 240 ml in a holding chamber. The volume of the holding chamber is a minor fraction of a deep inspiratory breath (>2 liters). The chamber is designed so that during inhalation of the puff, ambient air is pulled into the chamber thereby pushing aerosol out of the chamber and deep into the lungs.

Blood sufficient to provide a minimum of 1 ml plasma was collected from 24 subjects in heparinized tubes at 30 and 15 minutes prior to insulin dosing and 0 (just prior to insulin dosing), 5, 10, 20, 30, 45, 60, 90, 120, 180, 240, 300 and 360 minutes after the start of the inhalation. The insulin bioavailabilities for samples taken at 360 minutes are shown in Table 1 as uU.min/mL (microunits of insulin per milliliter of blood plasma). These figures shown that a low initial flow rate followed by a higher flow rate provided for higher bioavailability of insulin than the constant higher flow rate (an average of 11% increase for the condition of case B as compared to case A The combination of low initial flow rate and small particle size further increased bioavailability (an average of a 242% increase for case C as compared with case B).

TABLE I

| | AUC360 (uU.min/mL) | | | AUC360 Ratio | |
|---|---|---|---|---|---|
| Subject Number | A no ramp large PSD | B ramp large PSD | C ramp small PSD | B/A Effect of Ramp | C/B Effect of PSD |
| 50180001 | 728 | 2300 | 4403 | 3.16 | 1.91 |
| 50180002 | 1187 | 1394 | 2704 | 1.17 | 1.94 |
| 50180003 | 944 | 1191 | 3490 | 1.26 | 2.93 |
| 50180004 | 1973 | 737 | 2600 | 0.37 | 3.53 |
| 50180005 | 3362 | 4243 | 7294 | 1.26 | 1.72 |
| 50180006 | 2217 | 2948 | 5452 | 1.33 | 1.85 |
| 50180007 | 1507 | 1017 | 2554 | 0.67 | 2.51 |
| 50180008 | 795 | 996 | 1900 | 1.25 | 1.91 |
| 50180009 | 2447 | 2250 | 3593 | 0.92 | 1.60 |
| 50180010 | 5644 | 5613 | 12474 | 0.99 | 2.22 |
| 50180011 | 1714 | 441 | 2206 | 0.26 | 5.00 |
| 50180012 | 523 | 393 | 2602 | 0.75 | 6.62 |
| 50180013 | 1036 | 1129 | 1794 | 1.09 | 1.59 |
| 50180014 | 2823 | 2834 | 4468 | 1.00 | 1.58 |

TABLE I-continued

| | AUC360 (uU.min/mL) | | | AUC360 Ratio | |
|---|---|---|---|---|---|
| Subject Number | A no ramp large PSD | B ramp large PSD | C ramp small PSD | B/A Effect of Ramp | C/B Effect of PSD |
| 50180015 | 1835 | 2038 | 2488 | 1.11 | 1.22 |
| 50180016 | 1623 | 1102 | 2636 | 0.68 | 2.39 |
| 50180018 | 2317 | 1965 | 5561 | 0.85 | 2.83 |
| 50180019 | 690 | 1175 | 2373 | 1.70 | 2.02 |
| 50180020 | 1399 | 1113 | 3045 | 0.80 | 2.74 |
| 50180021 | 681 | 834 | 2157 | 1.22 | 2.59 |
| 50180022 | 1093 | 2137 | 3564 | 1.96 | 1.67 |
| 50180023 | 1931 | 2157 | 5098 | 1.12 | 2.36 |
| 50180024 | 255 | 134 | 183 | 0.53 | 1.37 |
| 50180028 | 731 | 822 | 1627 | 1.12 | 1.98 |
| AVG | 1644 | 1707 | 3594 | 1.11 | 2.42 |
| STD | 1158 | 1263 | 2440 | 0.58 | 1.20 |
| RSD | 70 | 74 | 68 | 52 | 50 |

The disclosure of each publication, patent or patent application mentioned in this specification is incorporated by reference herein to the same extent as if each individual publication, patent or patent application were specifically and individually indicated to be incorporated by reference.

We claim:

1. A device for controlling the delivery of an aerosolized active agent to the lungs of a human patient, said device comprising a valve that provides a high flow resistance of at least 0.4 $(cm\ H_2O)^{1/2}/SLM$ in the inhalation direction at the onset of the patient's inhalation and that subsequently opens during the inhalation to provide a lower flow resistance, wherein the lower flow resistance allows for a higher flow rate through the device.

2. A device according to claim 1 wherein the high flow resistance is a resistance of between 0.4 and 2 $(cm\ H_2O)^{1/2}/SLM$.

3. The device of claim 1 wherein the lower flow resistance is a resistance between 0 and 0.3 $(cm\ H_2O)^{1/2}/SLM$.

4. The device of claim 1 wherein the high flow resistance corresponds to a flow rate of 15 liters per minute or less.

5. The device of claim 1 wherein the lower flow resistance corresponds to a flow rate of 15-80 liters per minute.

6. The device of claim 1 wherein the high flow resistance is provided for an initial time period of less than 10 seconds.

7. The device of claim 1 wherein the high flow resistance is provided for an initial time period of less than 5 seconds.

8. A device for controlling the delivery of an aerosolized active agent to the lungs of a human patient, said device comprising a valve that provides a high flow resistance in the inhalation direction at the onset of the patient's inhalation and which corresponds to a flow rate of about 15 liters per minute or less and that subsequently opens during the inhalation to provide a lower flow resistance which corresponds to a higher flow rate.

9. The device of claim 8 wherein the lower flow resistance corresponds to a flow rate of between about 15 and 80 liters per minute.

10. The device of claim 8 wherein the high flow resistance is a resistance of between about 0.4 and 2 $(cm\ H_2O)^{14}/SLM$.

11. The device of claim 8 wherein the high flow resistance is provided for an initial time period of less than about 10 seconds.

12. A device for controlling the delivery of an aerosolized active agent to the lungs of a human patient, said device comprising a valve that is adapted to provide a first flow resistance in the inhalation direction at the onset of the patient's inhalation and that subsequently opens during the inhalation to provide a second flow resistance, the second flow resistance being less than the first flow resistance, wherein the second flow resistance allows for a higher flow rate.

13. The device of claim 12 wherein the first flow rate is provided for an initial time period of less than about 10 seconds.

14. The device of claim 12 wherein the first flow rate is less than about 15 liters per minute.

15. The device of claim 14 wherein the second flow rate is between about 15 and 80 liters per minute.

16. The device of claim 12 wherein the first flow resistance provides a first flow rate and wherein the second flow resistance provides a second flow rate.

* * * * *